(12) United States Patent
Ahmed

(10) Patent No.: US 7,260,402 B1
(45) Date of Patent: Aug. 21, 2007

(54) APPARATUS FOR AND METHOD OF CREATING AND TRANSMITTING A PRESCRIPTION TO A DRUG DISPENSING LOCATION

(75) Inventor: Omar Ahmed, Claremont, CA (US)

(73) Assignee: OA Systems, Inc., Rancho Cucamonga, CA (US)

( * ) Notice: Subject to any disclaimer, the term of this patent is extended or adjusted under 35 U.S.C. 154(b) by 291 days.

(21) Appl. No.: 10/448,965

(22) Filed: May 30, 2003

Related U.S. Application Data

(60) Provisional application No. 60/384,954, filed on Jun. 3, 2002.

(51) Int. Cl.
*H04Q 7/20* (2006.01)
*H04M 1/00* (2006.01)

(52) U.S. Cl. .................................. 455/445; 455/556.2

(58) Field of Classification Search ................ 455/445, 455/556.2, 558, 404, 567, 100; 705/2; 340/539.11, 340/573.1, 539.1, 539.12, 539.13, 573.4, 340/540; 379/38, 40, 45, 51, 37, 41, 42
See application file for complete search history.

(56) References Cited

U.S. PATENT DOCUMENTS

| | | | |
|---|---|---|---|
| 5,737,539 A | 4/1998 | Edelson et al. | |
| 5,845,255 A | 12/1998 | Mayaud | |
| 5,884,273 A | 3/1999 | Sattizahn et al. | |
| D415,203 S | 10/1999 | Sherman | |
| 5,963,136 A | 10/1999 | O'Brien | |
| 5,963,453 A | 10/1999 | East | |
| 6,056,322 A | 5/2000 | Lupi | |
| 6,150,942 A | 11/2000 | O'Brien | |
| 6,389,461 B1 | 5/2002 | Shah | |
| 2001/0002448 A1 | 5/2001 | Wilson et al. | |
| 2001/0016812 A1 | 8/2001 | Lin et al. | |
| 2004/0157612 A1* | 8/2004 | Kim | 455/445 |
| 2004/0220830 A1* | 11/2004 | Moreton et al. | 705/2 |
| 2004/0225527 A1* | 11/2004 | Holz | 705/2 |
| 2004/0235446 A1* | 11/2004 | Flaherty et al. | 455/352 |
| 2005/0060198 A1* | 3/2005 | Bayne | 705/2 |

* cited by examiner

*Primary Examiner*—Naghmeh Mehrpour
(74) *Attorney, Agent, or Firm*—John J. Connors; Connors & Assoc. Inc.

(57) ABSTRACT

A medical practitioner creates a prescription using a hand-held portable device. The device uses a plurality of interactive screens that display information such as lists of drugs. The medical practitioner enters patient information and selects from the list the desired drug to be prescribed. The device gives the practitioner access to a drug database that may be limited by the drugs prescribable by the medical practitioner. Once a prescription is created, the practitioner can select a drug dispensing location and communicate the prescription to this location. The drug database and the drug dispensing locations may be stored in a removable memory.

69 Claims, 11 Drawing Sheets

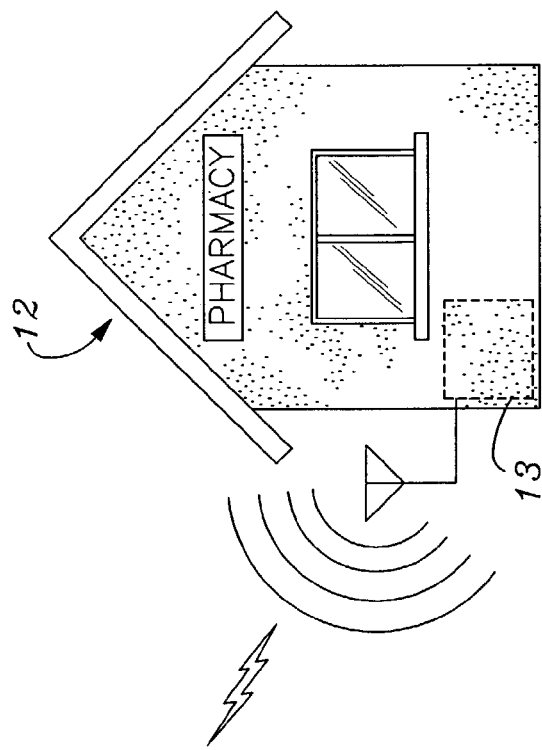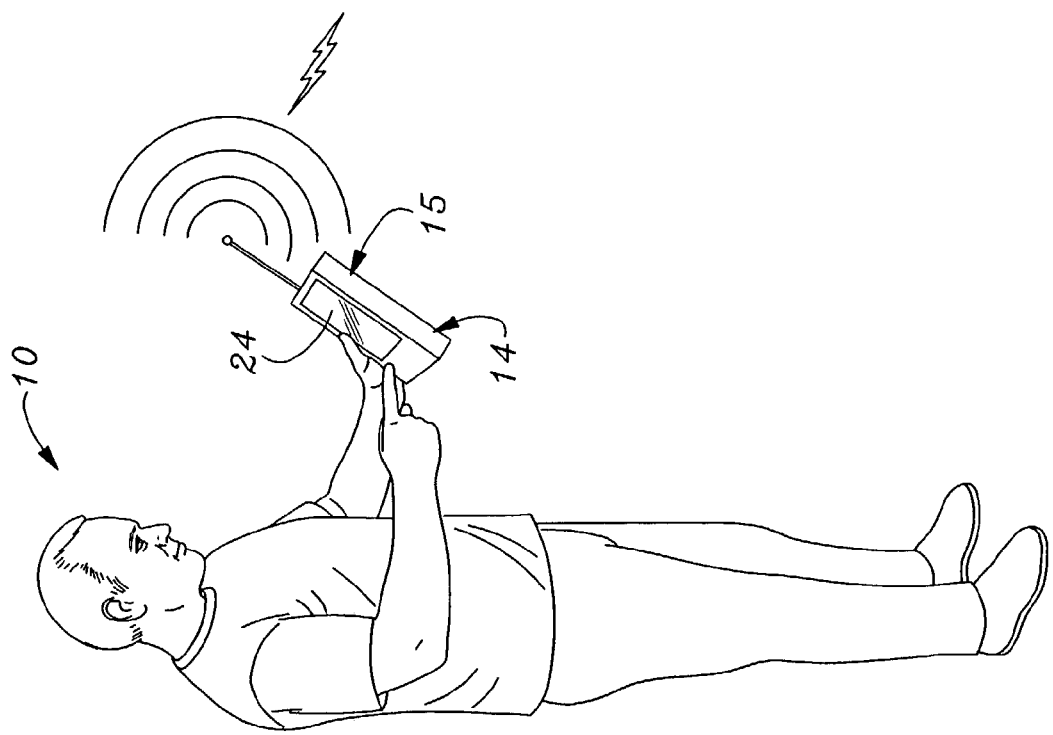
Fig. 1

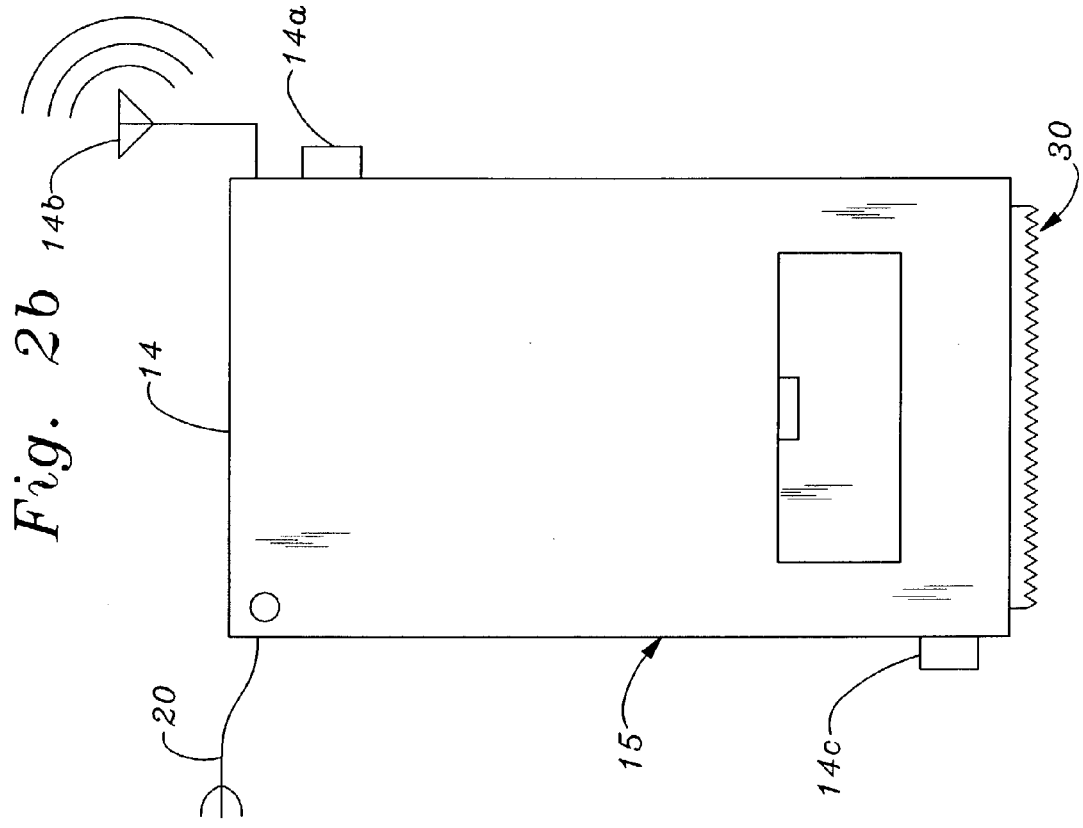
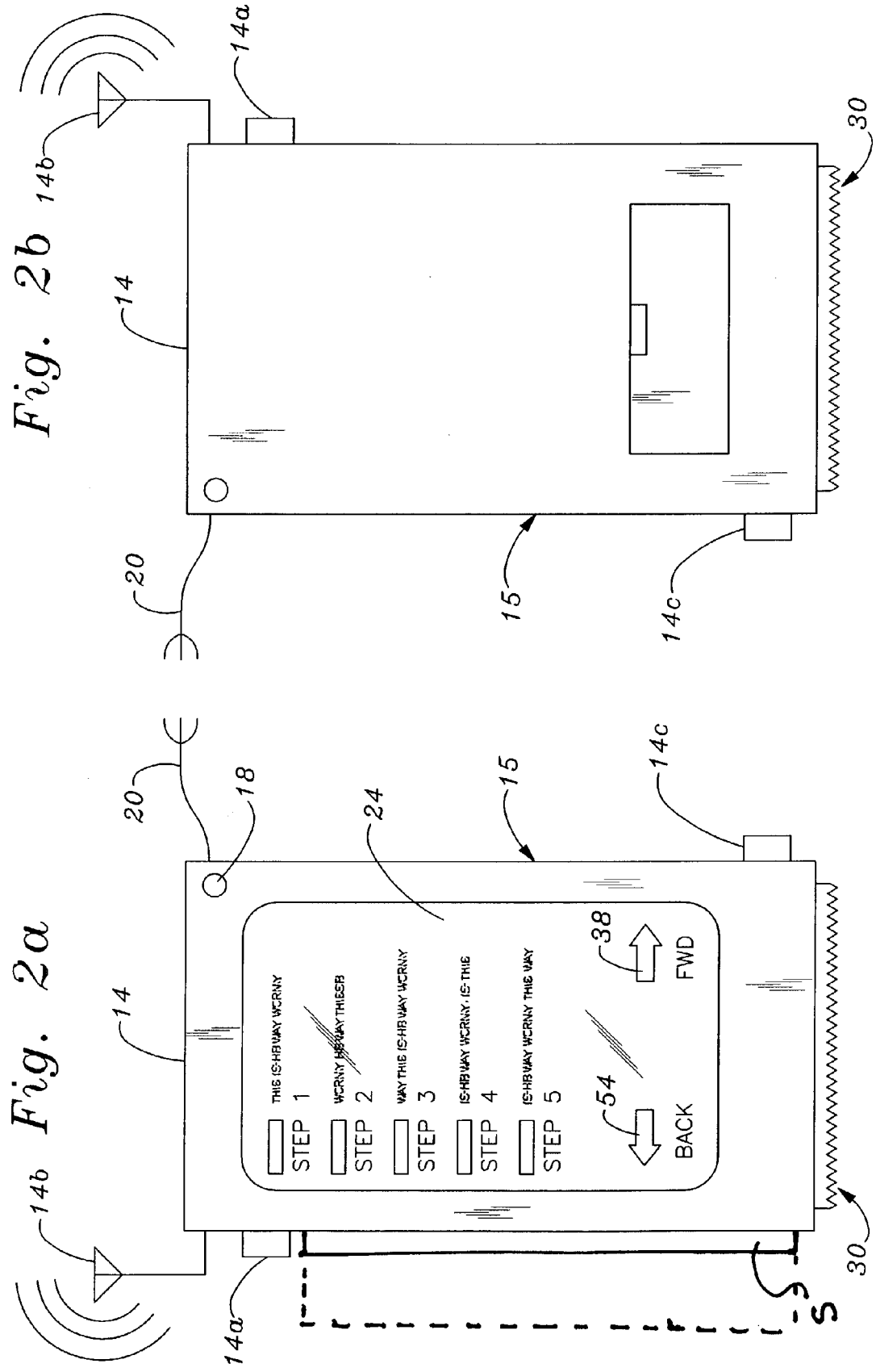

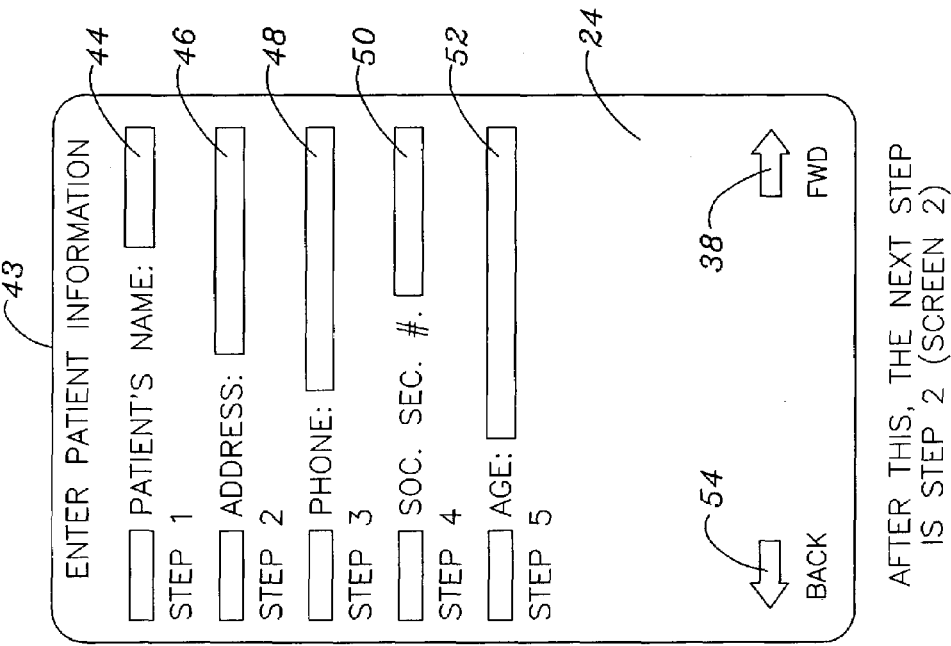
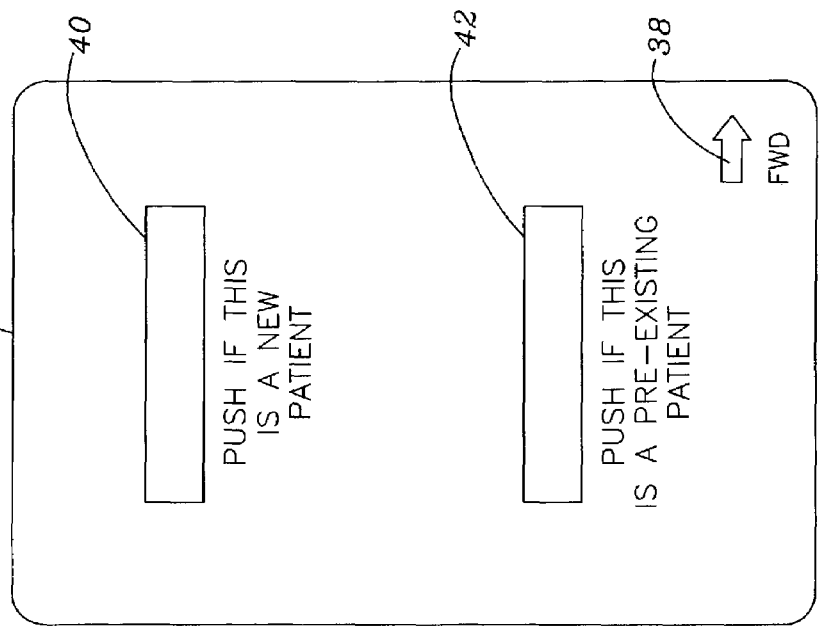

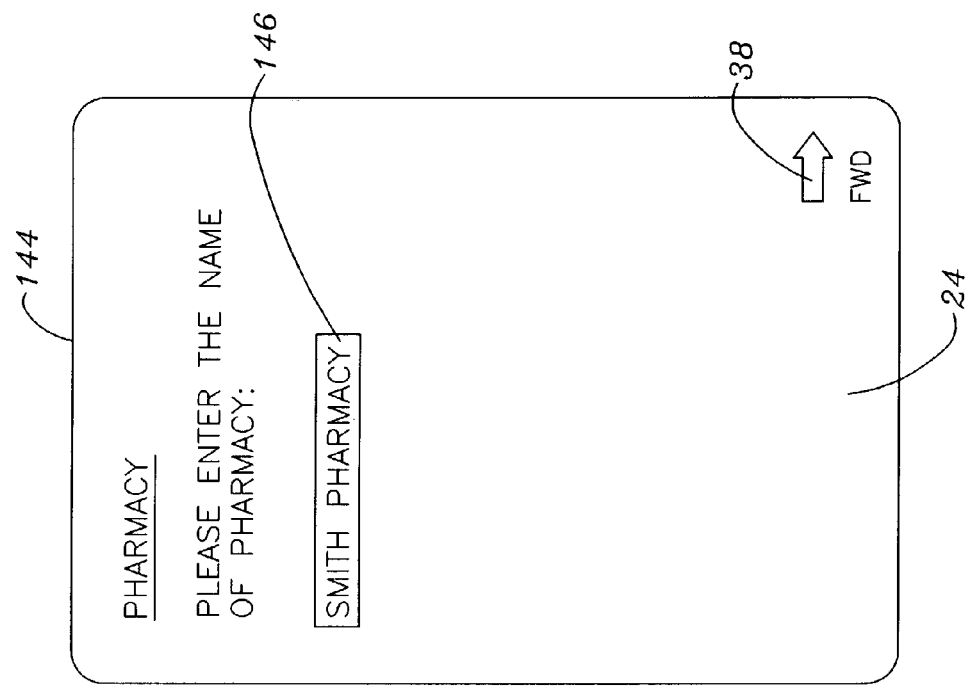
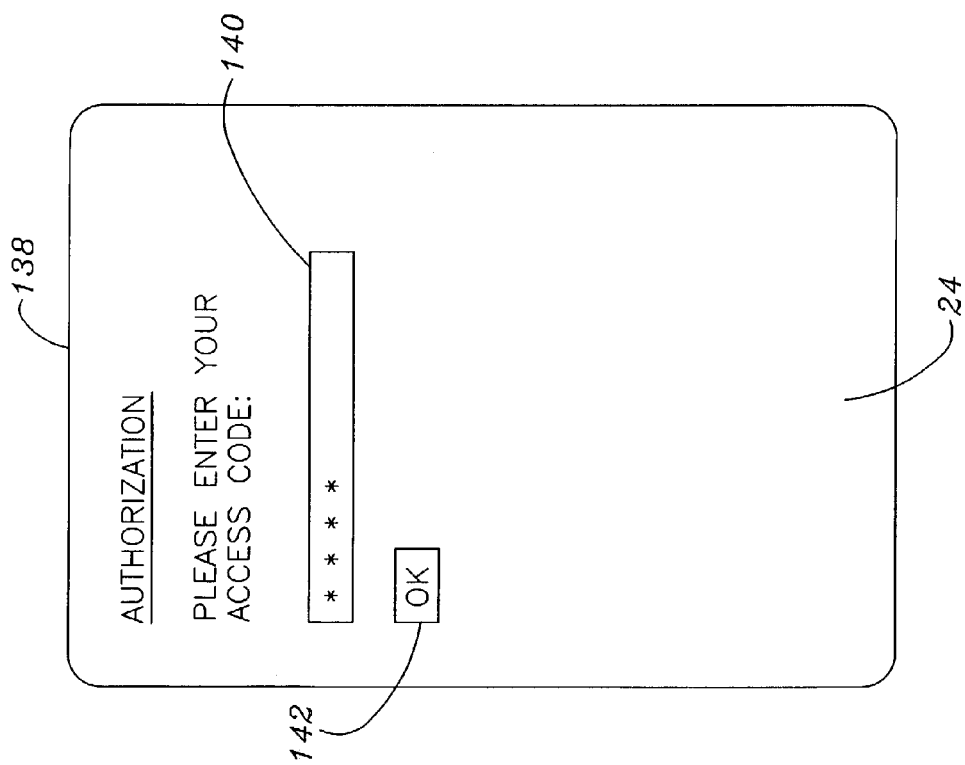

APPARATUS FOR AND METHOD OF CREATING AND TRANSMITTING A PRESCRIPTION TO A DRUG DISPENSING LOCATION

RELATED PATENT APPLICATIONS & INCORPORATION BY REFERENCE

This application is a utility application based on U.S. provisional patent application Ser. No. 60/384,954, entitled "Apparatus For & Method Of Creating and Transmitting A Prescription To A Drug Dispensing Location," filed Jun. 3, 2002. This related application is incorporated herein by reference and made a part of this application. If any conflict arises between the disclosure of the invention in this utility application and that in the related provisional application, the disclosure in this utility application shall govern. Moreover, the inventor incorporates herein by reference any and all U.S. patents, U.S. patent applications, and other documents cited or referred to in this application or cited or referred to in the U.S. patents and U.S. patent applications incorporated herein by reference.

DEFINITIONS

The words "comprising," "having," and "including," and other forms thereof, are intended to be equivalent in meaning and be open ended in that an item or items following any one of these words is not meant to be an exhaustive listing of such item or items, or meant to be limited to only the listed item or items.

BACKGROUND OF INVENTION

A point of care such as a doctor's office typically lies some distance from a drug dispensing location such as a pharmacy. A patient typically receives a prescription at the doctor's office and then travels to the pharmacy where the prescription is filled. Presently, a doctor creates a prescription by learning of the patient's symptoms, diagnosing the aliment, and then choosing drugs that will cure the aliment, or control its symptoms. Typically, a doctor hand writes a prescription. Frequently a pharmacist misinterprets the doctor's handwriting and the wrong drug is dispensed to the patient. Consumption of an improper drug can lead to patient illness and sometimes death. According to the 1999 Institute of Medicine Report, there were about one million serious medication errors per year in the United States because of illegible handwriting on prescriptions, misplaced decimal points, and missed drug interactions and allergies. Thus, there is a need to create prescriptions that are legible and accurate. There is also a need to communicate the prescription directly to the pharmacy.

SUMMARY OF INVENTION

This invention has one or more features as discussed subsequently herein. After reading the following section entitled "DETAILED DESCRIPTION OF SOME EMBODIMENTS OF THIS INVENTION," one will understand how the features of this invention provide its benefits. The benefits of this invention include, but are not limited to: creating and transmitting accurately a prescription from a prescriber (herein medical practitioner) to a remote drug dispensing location, providing a portable and convenient to use hand-held device for prescribing and transmitting prescriptions to a remote drug dispensing location, improving the accuracy of prescriptions by providing computerized means of creating and validating drug choices and by providing communication of the prescription directly from the medical practitioner to the drug dispensing location, and avoiding or at least significantly reducing human errors in connection with prescribing drugs.

Briefly, this invention includes a method of creating a prescription using a portable device. The portable device employs a graphical user interface enabling the medical practitioner to select one or more drugs from a list of drugs and transmit the selected drug or drugs as a prescription to a remote drug dispensing location. The list may be a drug database defined by the geographical location of the medical practitioner or the field of practice of the medical practitioner, or both. A list of drugs may be displayed on the portable device for viewing by the medical practitioner. The device enables the medical practitioner to select the desired prescribed drug from this list. Optionally, the list may be based on specific aliments or symptoms of a patient that the medical practitioner enters into the device that is programmed to recommend one or more drugs to be used to treat these symptoms. A medical practitioner creates a prescription by selecting drugs from the list and providing at least sufficient information to identify the patient. Other patient data that is considered confidential or private and access only by authorized personnel. For example, this patient data may be encrypted and only accessed by those having decrypting software, or the data may be in a secured data bank that can only be accessed using a password or other means for identifying authorized users. The device transmits the prescription to a computer, for example, and the computer transmits the prescription to the drug dispensing location using a global computer network, i.e., the Internet. Alternately, or in conjunction with the Internet, a care giving facility may use an intranet where private patient data is stored on the intranet's server.

One or more of the following steps are conducted in practicing the method of this invention:
  (1) acquiring patient data,
  (2) acquiring patient aliment or symptoms,
  (3) diagnosing patient aliment or symptoms,
  (4) selecting drugs from a group of drugs defined by the aliments, or symptoms, or medical practitioner's geographical location of practice, or the medical practitioner's field of practice,
  (5) deriving a prescription from the selection,
  (6) communicating the prescription to the drug dispensing location,
  (7) querying whether patient information is available on an accessible database,
  (8) inputting patient information if the patient information is not available on the accessible database.

In one embodiment of the method of this invention, its steps include identifying patient symptoms, inputting the patient symptoms in to the device, providing a list of drugs associated with treating said symptoms, and selecting at least one drug from the list. In another embodiment of the method of this invention, its steps include identifying a patient aliment, inputting the patient aliment in to the device, providing a list of drugs associated with treating said aliment, and selecting at least one drug from the list.

Without limiting the scope of this invention as expressed by the claims that follow, some, but not necessarily all, of its features are:

One, this invention includes a system for creating a prescription by a medical practitioner and communicating this prescription to a remote drug dispensing location. The system may comprise a portable, hand held device, a communication link that transmits the selected drug prescription and patient information to a selected drug dispensing location, and a data receiver at the remote drug dispensing location that receives the selected drug and patient information. The medical practitioner may be certified to practice in a specific medical field and the listing of drugs may be limited to the practitioner's specific medical field. The system may include a node element in communication with the portable, hand held device that receives the selected drug prescription and patient information and transmits the drug prescription and patient information to the selected drug dispensing location. It may also include a computer that receives the selected drug prescription and patient information and transmits via a network the drug prescription and patient information to the selected drug dispensing location. The listing of a plurality of prescription drugs applicable to the specific medical field may be transmitted from a remote location to the device. One or more drug dispensing locations may be transmitted from these remote locations to the device. One or more drug dispensing locations may be selected based on a geographical region. The communication link may be hard wired or wireless, for example, a radio transmitter, an infrared transmitter, a wired transmitter, or an ultrasonic transmitter.

Two, the portable, hand held device of this invention may have (i) a display, (ii) a memory that may store (a) a listing of a plurality of prescription drugs, and (b) one or more drug dispensing locations, and (iii) a data input mechanism that enables the practitioner to identify a patient, select a drug dispensing location, select from the listing one or more of the listed prescription drugs to be dispensed at the selected drug dispensing location, and to enter specific dose for the selected prescription drug, The patient's name and other data such as previous prescriptions, aliments, symptoms, etc. may be stored in the memory of the portable, hand held device or at a remote, accessible location. The device may have a removable memory that stores the listing of a plurality of prescription drugs, one or more drug dispensing locations, or other useful information or data. The data input mechanism may be a keyboard. The portable, hand held device may have a plurality of interactive screens retained in the memory for displayed by the display screen. It may also include a selector device enabling the medical practitioner to move from one screen to another.

These features are not listed in any rank order nor is this list intended to be exhaustive.

DESCRIPTION OF DRAWING

Some embodiments of this invention, illustrating all its features, will now be discussed in detail. These embodiments depict the novel and non-obvious device, system and method of this invention as shown in the accompanying drawing, which is for illustrative purposes only. This drawing includes the following figures (Figs.), with like numerals indicating like parts:

FIG. 1 is a schematic view illustrating a medical practitioner transmitting a prescription from the medical practitioner's office to a pharmacy at a remote location using one embodiment of the portable, hand held device of this invention for creating a prescription.

FIG. 2a is front view of the portable, hand held device shown in FIG. 1.

FIG. 2b is a back view of the device shown in FIG. 2a.

FIG. 7 is an initial display screen of the device shown in FIG. 1.

FIG. 8 is a patient data input screen of the device shown in FIG. 1.

FIG. 17 is an authorization screen of the device shown in FIG. 1.

FIG. 18 is pharmacy search screen of the device shown in FIG. 1.

DETAILED DESCRIPTION OF SOME
EMBODIMENTS OF THIS INVENTION

Typically, a patient goes to a medical practitioner 10 at his or her office to have an aliment diagnosed, and to receive a prescription that is dispensed at a drug dispensing location, such as a pharmacy 12. The medical practitioner's office is usually some distance from the pharmacy 12. Referring to FIG. 1, in accordance with this invention, a handheld, portable device 14 is used by the medical practitioner 10 to create and communicate a prescription to the pharmacy 12 in a manner that eliminates or reduces the likelihood of errors. The pharmacy 12 has a data receiver 13 such as a computer that receives the prescription from the device 14. The medical practitioner 10 may take the device 14 along with him as he attends to patients, and create the prescription once he has determined what drugs he wishes to prescribe. Once a prescription is created, it may be saved and stored in a patient data file either in the device or a secure data bank.

Figure 3:
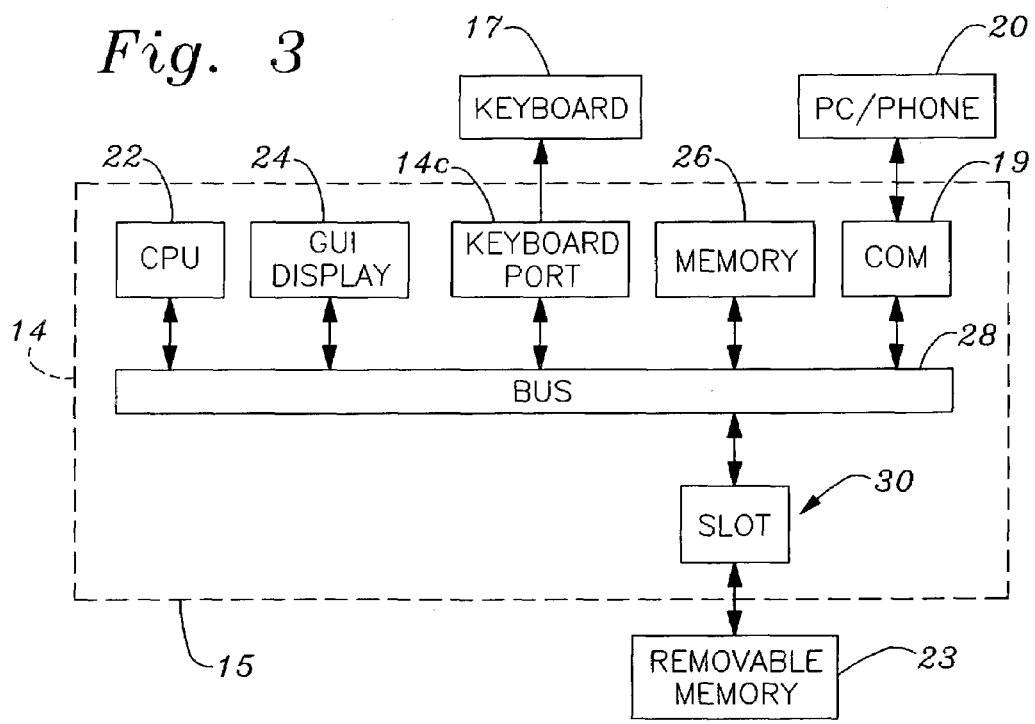
FIG. 3 is schematic diagram of the portable, hand held device of this invention shown in FIG. 1.

In one preferred embodiment, such as the one shown in FIGS. 2a, 2b, and 3, a handheld, portable device 14 may be carried by a medical practitioner as he or she attends patients. The device 14 has a case 15 carrying external components such as an on/off button 14a, an ac adapter 14b, a light emitting diode (LED) 18, and a liquid crystal display 24 used as a touch screen type graphical user interface (GUI). The light emitting diode (LED) 18, when illuminated, is used to indicate that the device 14 is on. The case 15 has a slot 30 where a removable memory card 23 is inserted. Referring to FIG. 3, the case 15 encloses internal elements such as a processor (CPU) 22, input port 14c, a stationary memory 26, and an output port 19 adapted to be linked to a communication system for transmission of data to the pharmacy 12. The output port 19 allows the device 14 to connect via a communication link 20 connected to a phone jack or a personal computer (pc), for example, to allow communication with the data receiver 13 at the pharmacy 12. The memory 26 is used to store data for use by the device's processor 22. A bus 28 connects the components and elements of the device 14.

Figure 4:
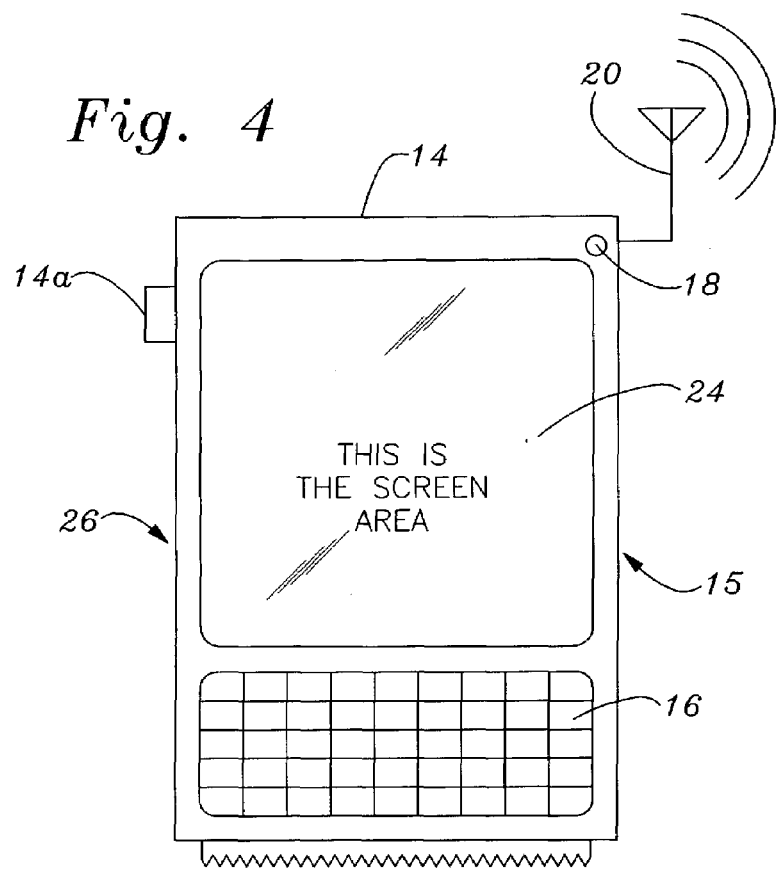
FIG. 4 is front view of a second embodiment of the portable, hand held device of this invention with an integrated keypad.

In one preferred embodiment, the device 14 has an attachable keyboard 17. The keyboard 17 attaches to the device 14 through the input port 14c. Referring to FIG. 4, in another preferred embodiment, a keypad 16 is integrated with case 15 of the device 14. In one embodiment, the device 14 connects to a wide area network such as the internet (World Wide Web) using the communication link 20 and transmits the prescription over a phone line, for example. The device 14 establishes the communication link 20 with an internet service provider (ISP). The device 14 uses an internet browser, such as, Internet Explorer® produced by Microsoft Corporation of Redmond, Wash., to browse and to transfer the prescription to the pharmacy 12. Once the communication link 20 is established, a transmission control protocol/internet protocol (TCP/IP) is used to send information between the ISP and the device 14. The ISP allows access to the Internet and the prescription is sent to the pharmacy 12 through e-mail or a file transfer protocol (FTP). The methods described to connect to the Internet and transfer files between locations are merely illustrative, and are not meant to be an exhaustive description of all possible methods. The prescription is uploaded to the personal computer (pc), for example, where it is then transmitted to the pharmacy. Typically, the personal computer (pc) transmits the prescription to the pharmacy through the Internet.

Figure 5:
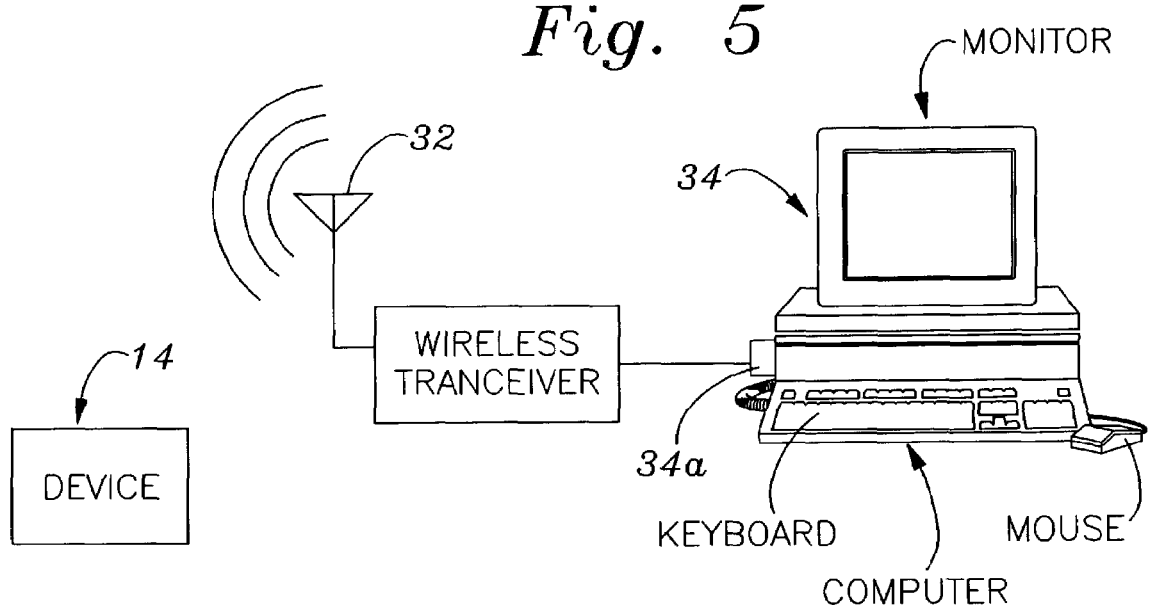
FIG. 5 is schematic view illustrating the device, a wireless node, and a computer.

Referring to FIG. 5, in another embodiment, the device 14 uses the communication link 20 to connect to a computer 34 through the computer's universal serial bus (USB) port 34a, via wireless communication with the computer. A node element, such as a wireless transceiver 32, interfaces with the computer 34 through the USB port 34a. In general, a node element is employed in a network and is a connection point for data transmissions. An example of a wireless transceiver is the AIRONET AIR-AP342E2R produced by Cisco Technology Inc. of San Jose, Calif. The wireless transceiver 32 wirelessly receives transmissions from the device 14, such as, the prescription for the patient, and transmits the prescription to the computer 34. The transceiver 32 may also receive data such as, drug dispensing locations and a drug database, from the computer 34 and transmit such data to the device 14. The device 14 then stores the locations and drug database in memory 26. Drug dispensing location data and drug databases may be downloaded to the computer 34 from the Internet. A service fee may be charged to a medical practitioner to update the drug dispensing locations and drug databases. Wireless transmission methods include infrared, ultrasonic and radio frequency.

In one embodiment, the drug databases do not contain a listing of all drugs produced, but rather, are limited to drugs available in the geographical region of the medical practitioner. For example, some drugs available in Europe are not available in the United States, and vice versa. Thus, a drug database designed for use in Europe may contain drugs that are not on a database for the United States.

In another embodiment, a drug database is limited to drugs available in a medical practitioner's field of practice. Typically, medical practitioners cannot prescribe drugs that are not associated with their practice. Limiting a drug database to those prescribable by the medical practitioner would eliminate confusion with other, non-prescribable drugs. Thus, drugs not prescribable by an individual medical practitioner are not available in the drug database.

In one embodiment, removable memory cards are used to store drug databases. Removable memory cards may also be used to store drug dispensing locations database. An example of the removable memory card 23 is the Microdrive produced by International Business Machines Corporation of Armonk, N.Y. There are specific memory cards 23 available based upon the medical practitioner's field of practice and his location of practice. Referring to FIG. 3, the removable memory cards 23 are connected to the device 14 through a memory card slot 30 that connects to the bus 28. In one embodiment a single removable memory card 23 may store both the drug dispensing locations database and the drug databases.

Figure 6:
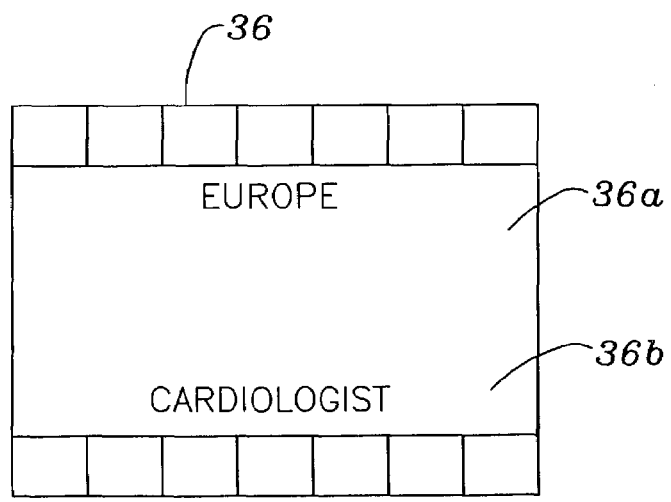
FIG. 6 is front view of a removable memory card for the device shown in FIG. 1.

Referring to FIG. 6, in one preferred embodiment, a single memory card 36 contains both the drug dispensing locations database, and the drug database. Markings on the exterior surface of the memory card 36 indicate the region 36a and the field of practice 36b of the memory card. In another embodiment, the drug dispensing locations database and the drug database are on different memory cards. In this embodiment, the device has a memory slot for each memory card.

In one embodiment, the device 14 displays a plurality of screens. The medical practitioner uses these screens to input, and select information that will be used to create a prescription. Typically, anyone of the displays is an interactive display where the medical practitioner uses, for example, a personal digital assistant (PDA) stylus pen, such as, the stylus pen produced by Palm, Inc. of Santa Clara, Calif.

FIG. 7 is a first display screen 37 of the device 14. A forward button 38 allows a medical practitioner to move forward between screens. The medical practitioner is queried whether the patient is a new patient 40, or a pre-existing patient 42. If the patient is a new patient, a new patient screen 43, as shown in FIG. 8, is presented with empty fields 44, 46, 48, 50, and 52, so the medical practitioner may enter patient data, such as, the patient's name 44, address 46, phone number 48, social security number 50, and age 52. Each display screen, except for the first, has a back button 54 that allows the medical practitioner to view and edit a previous screen.

Figure 10:
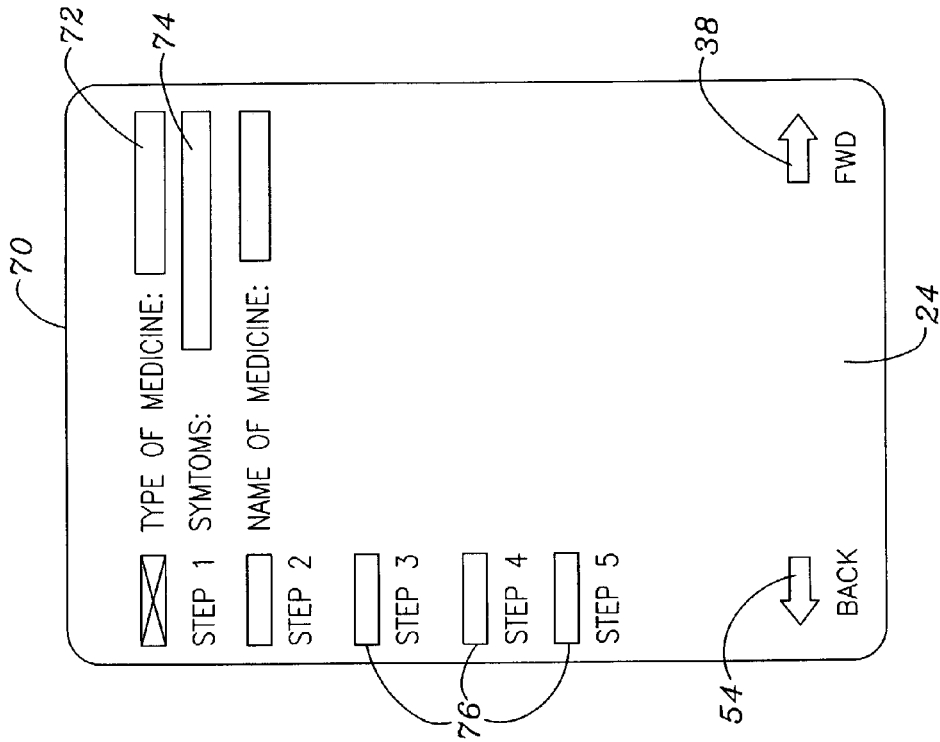
FIG. 10 is a symptoms/medicine input screen of the device shown in FIG. 1.
Figure 9:
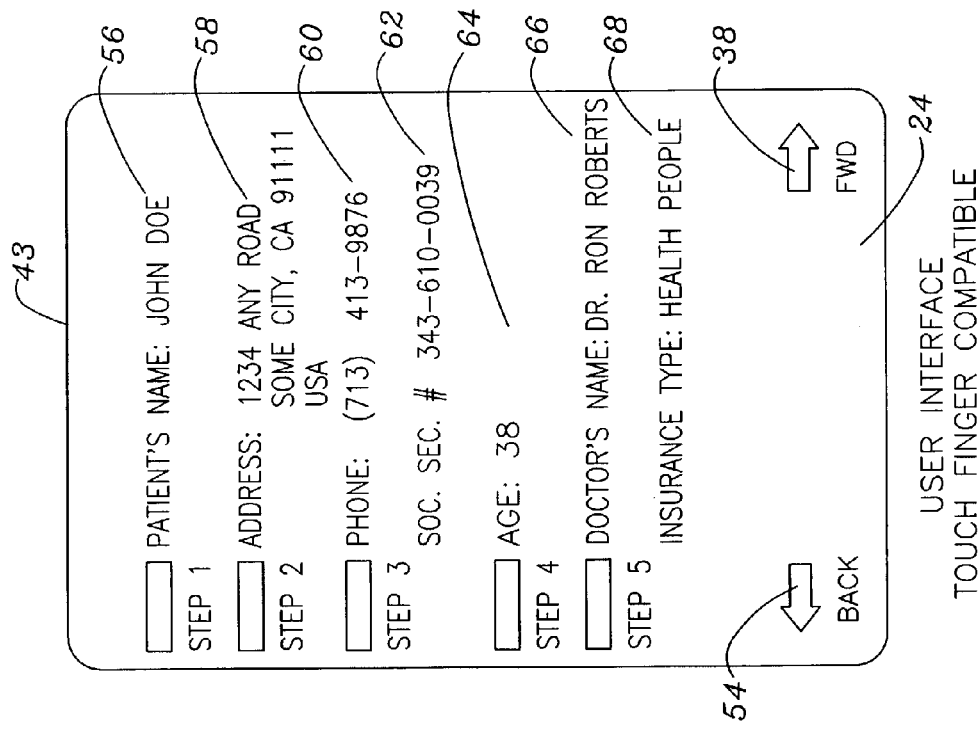
FIG. 9 is a patient data summary screen of the device shown in FIG. 1.

Once the patient data has been acquired, either as a result of a query from a database, or entered manually, the patient data is displayed, as is shown in FIG. 9. The patient's name 56, address 58, phone number 60, social security number 62, age 64, medical practitioner's name 66 and the patient's insurance carrier 68 are displayed. Pressing the forward button 38 displays the symptoms/medicine screen 70 shown in FIG. 10.

Figure 11:
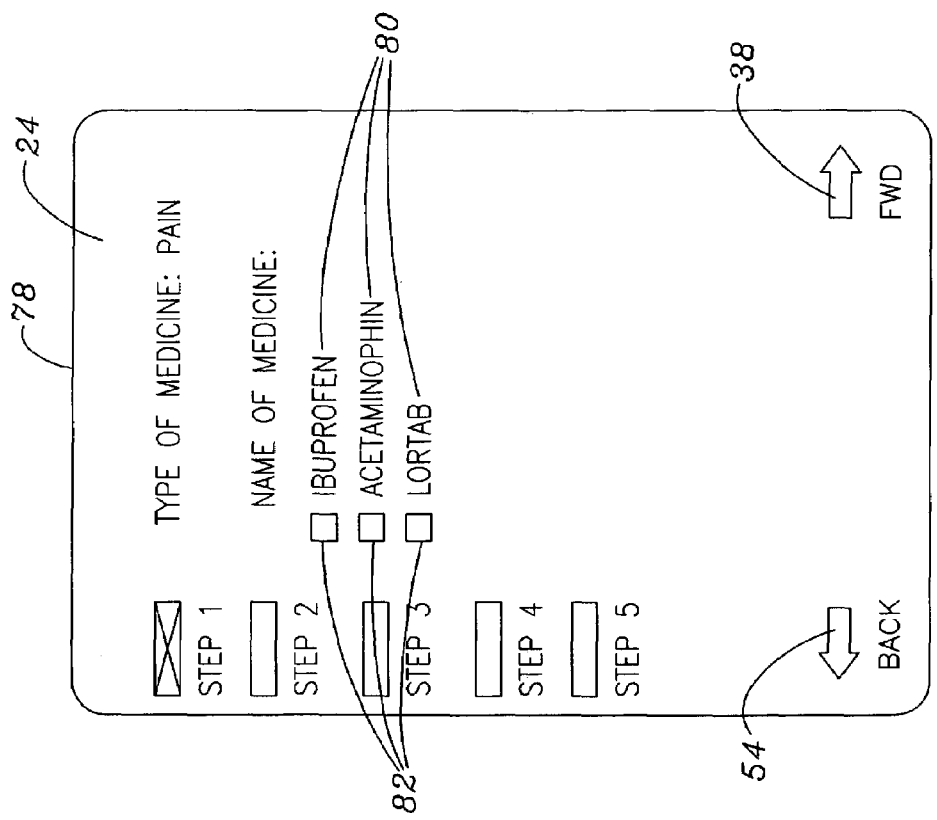
FIG. 11 is a type of medicine search results screen of the device shown in FIG. 1.

The symptoms/medicine screen 70 allows the medical practitioner to enter in the field 72 information such as, the type of medicine the medical practitioner wishes to prescribe, and to enter in the field 74 the symptoms of the patient. The type of medicine may be, for example, an analgesic. Such an entry into the type of medicine field 72 is used to perform a search of the drug database for drugs that are in this category of the type of medicine entered. The symptoms field is used to search the drug database for drugs that either cure or treat the symptoms entered. The results of the drug search are then displayed, allowing the medical practitioner to select which drug he or she wishes to prescribe as depicted in FIG. 11.

Figure 12:
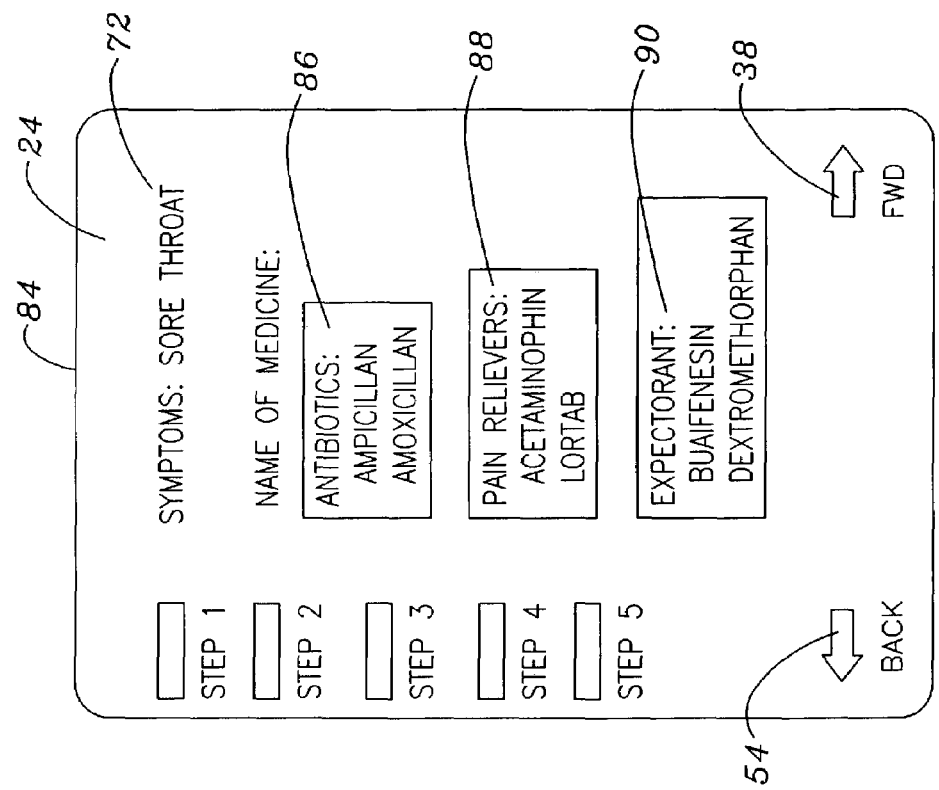
FIG. 12 is a symptoms results screen of the device shown in FIG. 1.

Entering the symptoms and/or type of medicine, is the first step in creating the prescription. Step indicators 76 shown in FIG. 10 let the medical practitioner know how he or she is progressing towards the completion of the prescription. The first step of creating the prescription is entering symptoms of the patient and/or the type of medicine to be prescribed. In one example of this embodiment, a medical practitioner enters "pain" into the type of medicine field. A search in the drug database is performed for drugs that are used to treat pain. FIG. 11 illustrates a results screen 78 that lists results 80 of a pain drug search. A medical practitioner selects a drug by selecting one of the radio buttons 82 next to of a listed drug. Similarly, FIG. 12 illustrates a search results screen 84 for an entry of sore throat in the symptoms field 72. The results may be categorized by the type of medicine, such as, antibiotics 86, pain reliever 88 and expectorant 90.

Figure 13:
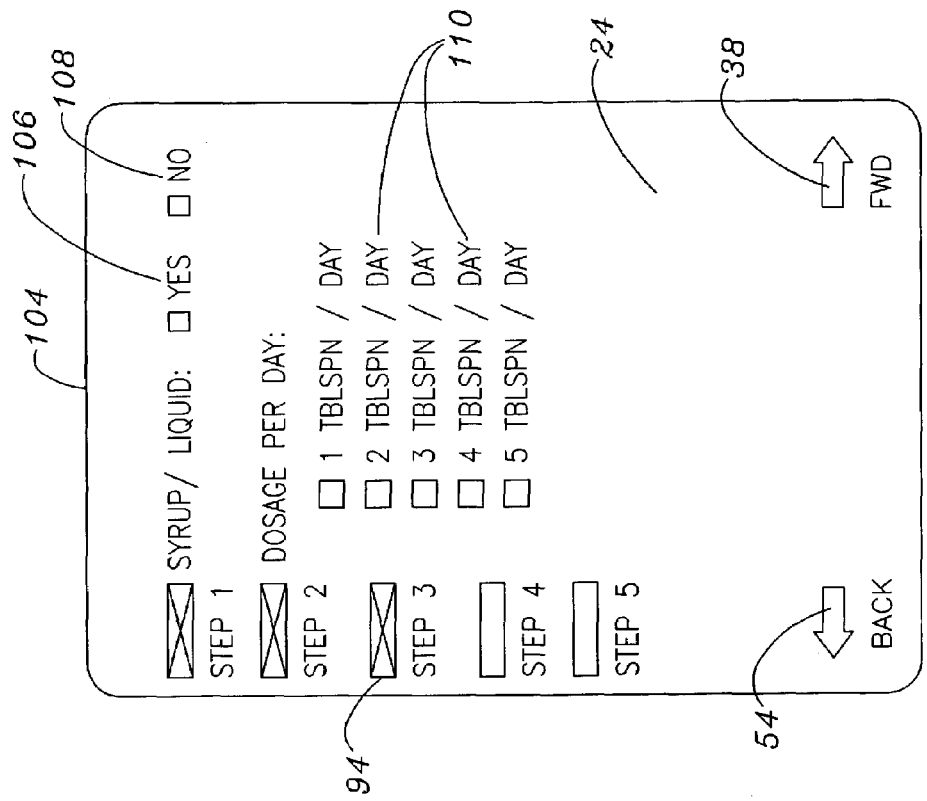
FIG. 13 is a tablet dosing screen of the device shown in FIG. 1.
Figure 14:
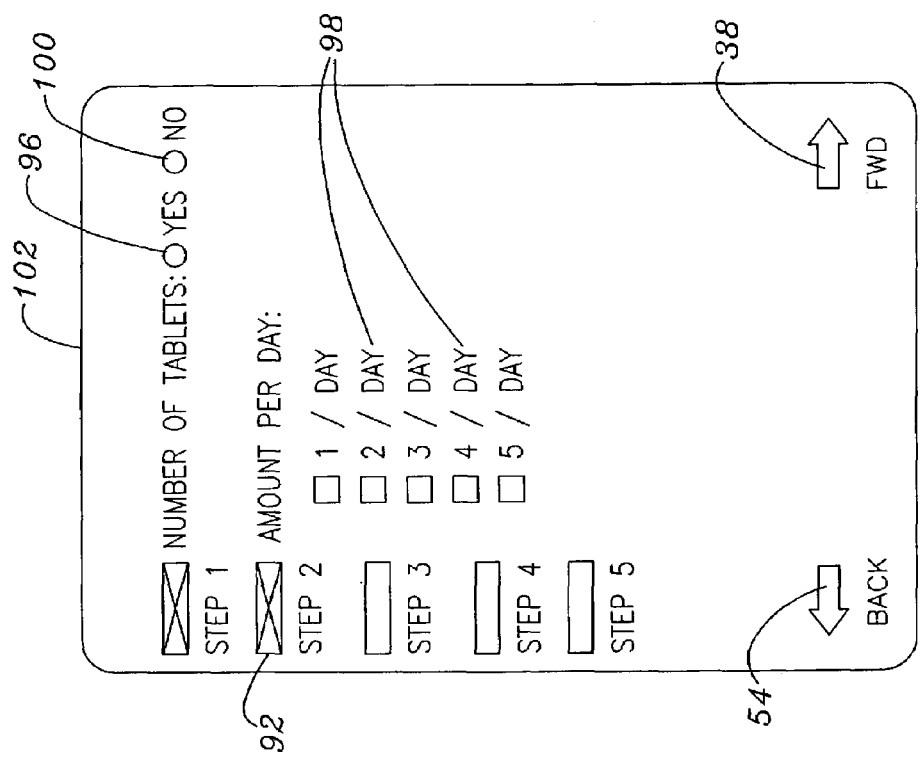
FIG. 14 is a syrup/liquid dosing screen of the device shown in FIG. 1.

The medical practitioner uses a dosing screen to enter dosing information for the selected drug. Dosing information provides the patient periodic instructions for taking the drug, and the amount of the drug that should be taken. Referring to FIGS. 13 and 14, the dosing screens display the second step button 92 and third step button 94 that are used in creating the prescription. FIG. 13 illustrates a dosing screen 102 for tablets. The medical practitioner indicates that he or she is prescribing tablets by selecting the yes button 96. A medical practitioner then selects the amount of tablets 98 that will be taken per day. It is contemplated that there may be variations in the dosing screen, such as, instructions to take two tablets as a first dose.

If the medical practitioner selects no button 100 in the tablet dosing screen 102, a syrup/liquid dosing screen 104 is displayed, as shown in FIG. 14. The medical practitioner first selects a yes button 106 to indicate he or she has a syrup/liquid drug to prescribe. The medical practitioner then selects the amount of tablespoons per day 110 of the syrup/liquid the patient is to take. It is contemplated that there may be variations in the syrup/liquid dosing screen 102, such as, using teaspoons as a liquid measure. If the medical practitioner does not wish to prescribe a syrup/liquid she selects the no button 108.

Figure 15:
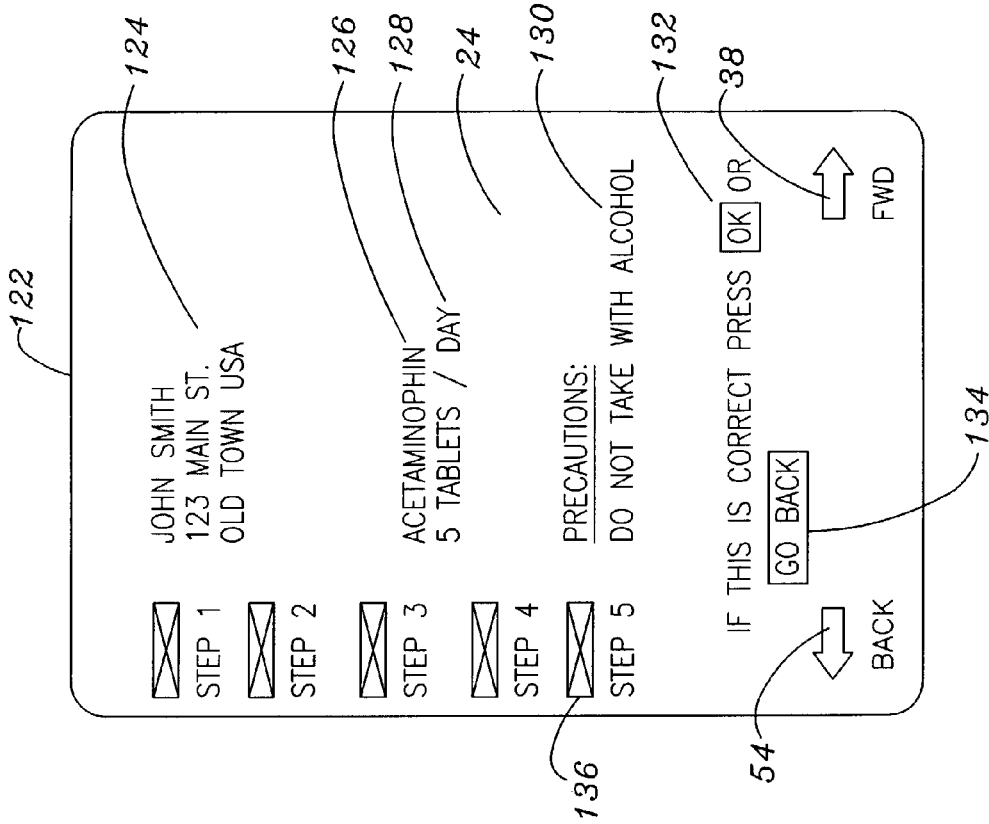
FIG. 15 is a screen for adding additional information, precautions, and medical practitioner's comments of the device shown in FIG. 1.

Referring to FIG. 15, a supplementary screen 112 allows the doctor to add supplemental information, such as, additional information 120, precautions 116 and doctor's comments 118. The supplemental screen 112 is called up by activating the fourth step button 114. Additional information can comprise suggestions regarding the dosing of the drug. For example, the additional information could be a recommendation that the entire prescription be finished. Precautions can comprise a statement that the drug should not be taken with alcohol, or other drugs. Medical practitioner's comments can comprise a statement that there are no refills for the prescription or list allergies that the patient has.

Figure 16:
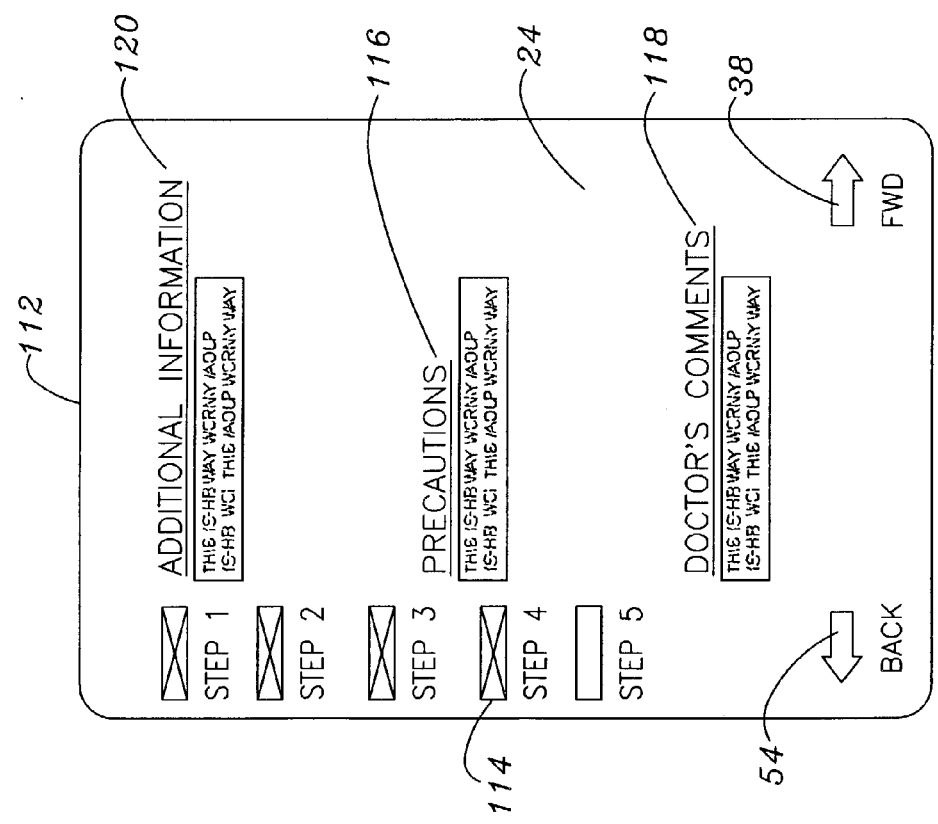
FIG. 16 is a prescription summary screen of the device shown in FIG. 1.

Referring to FIG. 16, after the prescription is completed, a summary screen 122 is displayed summarizing information from the previous screens. The summary screen 122 contains information, such as, the patient's name and address 124, the drug or drugs prescribed 126, the dosing 128, and any additional information, precautions 130 or comments from the medical practitioner. The medical practitioner is asked to confirm if the information is correct by pressing the ok field button 132 of the display. If the information is not correct, the doctor presses the go back field button 134 of the display to edit the information on the other screens. The summary screen 122 is the fifth step button 136 activated in creating the prescription.

In FIG. 17, after confirming that the information presented on the summary screen 122 is correct, an authorization screen 138 is displayed. The medical practitioner is required to enter an authorization code in an authorization code field 140. After entering the code, the doctor presses the ok field 142 of the display to move to pharmacy selection screen 144 (FIG. 18). Each doctor will be given a separate authorization code in order to avoid conflicts between doctors of the same name, thus avoiding errors and enhance security. Instead of an access code, a fingerprint, hand writing recognition, or key card may be used to provide access.

Figure 19:
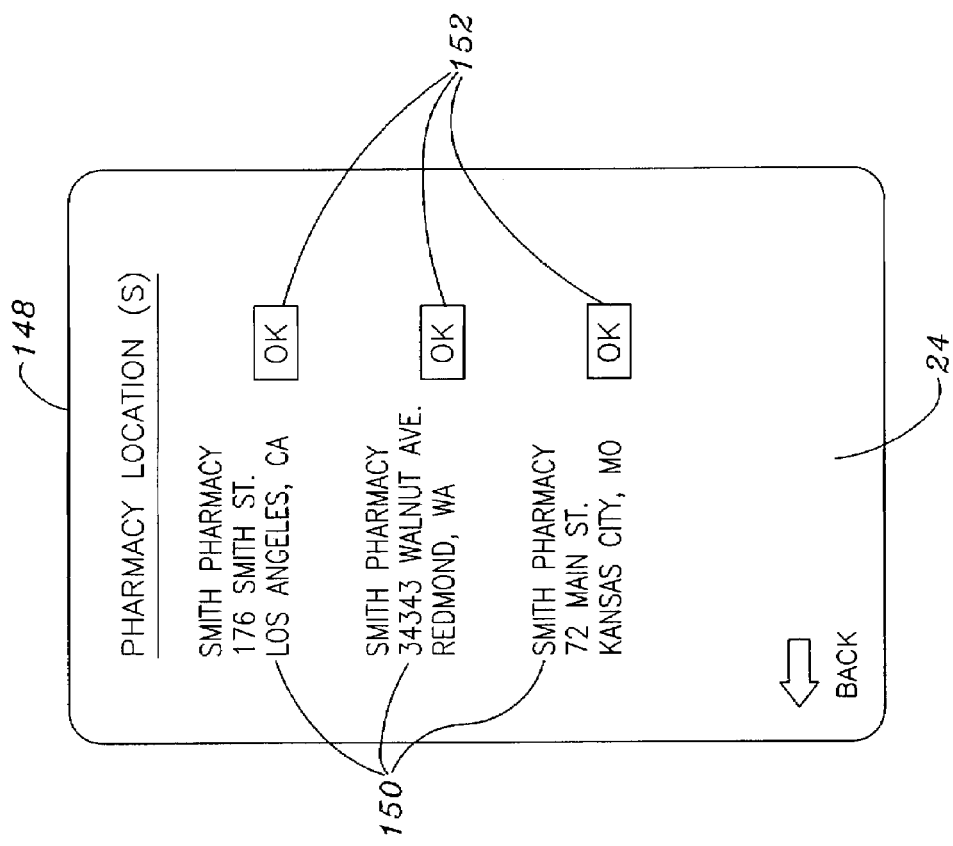
FIG. 19 is a pharmacy selection screen of the device shown in FIG. 1.

Referring to FIG. 18, a first pharmacy selection screen 144 is used to select the pharmacy that will dispense the prescription. The medical practitioner enters the pharmacy name into a data field 146. After entering the pharmacy name, the medical practitioner presses the forward button 38 and the second pharmacy selection screen 148 is displayed, as shown in FIG. 19. The drug dispensing location database is queried and a listing 150 of pharmacies that match the medical practitioner's entry is displayed.

Figure 20:
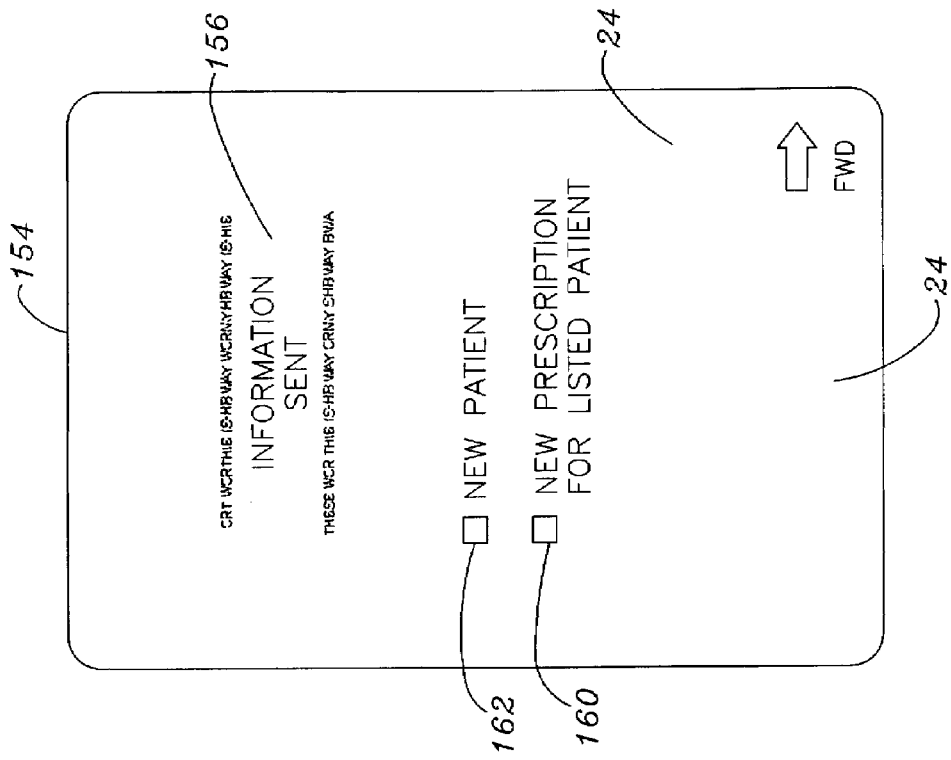
FIG. 20 is an information sent screen of the device shown in FIG. 1.

The medical practitioner selects a pharmacy from the second pharmacy location screen 148 by selecting the one ok field button 152 corresponding to the desired pharmacy. After selecting the desired pharmacy, an information sent screen 154 is displayed, as shown in FIG. 20. The information sent screen 154 displays in a field 156 a confirmation message that the prescription has been sent. The information sent screen 154 queries the medical practitioner if he or she wishes to create a new prescription for a patient already listed in a patient database. The medical practitioner selects that option by activating the new prescription for listed patient button 160. The medical practitioner may also create a prescription for a new patient by activating the new patient button 162.

Other Alternative Embodiments

It is contemplated that the device of this invention may also employ a wireless graphical interface connected to a remote computer. In this embodiment, the computer stores the drug and drug dispensing location databases. The device queries the databases stored on the computer to create a prescription and to select a drug dispensing location. The device is then used to instruct the computer to transmit the prescription to the drug dispensing location. It is also contemplated that the device may be connected to a printer that prints the prescription. A patient may then bring the printed prescription to a pharmacy to be filled.

In one alternate embodiment, instead using the removable memory card 23 to store private patient information, this private information may be stored in a database on a central server, for example on an intranet at a hospital. The private information may be encrypted so that only someone, such as the attending medical practitioner, having decrypting software may access this information. Encrypted private information may also be stored on a web server (internet) that the attending medical practitioner may access using decrypting software. This type of storage that uses file encryption maintains the security of this information. Such security may be needed in order to meet the Health Insurance Portability and Accountability Act (HIPAA), and to make the information more secure in case the portable device 14 is lost, stolen, or misused. In this embodiment, the memory card 23 will just store the drug databases and the drug dispensing databases.

In another alternate embodiment, as an optional feature, the portable device 14 may use a flexible, roll-away screen S (FIG. 2a) that will fit on the side of the device. For example, such a flexible screen S is produced by E Ink of Cambridge Mass. This screen S normally be rolled up like a scroll, and unwound (the screen is shown partially unwound in dotted lines) into a flat surface. This surface has a larger surface area than the liquid crystal display 24 on the device 14. Therefore, will give a larger image for the attending doctor to view.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

The invention claimed is:

1. A system for creating a prescription by a medical practitioner communicating said prescription to a remote drug dispensing location, said system comprising:
   a portable, hand held device having
   (i) a display,
   (ii) a memory that stores
      (a) a listing of a plurality of prescription drugs, and
      (b) one or more drug dispensing locations, and
   (iii) a data input mechanism that enables the practitioner to enter information identifying the patient, select a drug dispensing location, select from the listing one or more of the listed prescription drugs to be dispensed at said selected drug dispensing location, and to enter a specific dose for said selected prescription drug,
      a communication link that transmits said selected drug prescription and patient information to a selected drug dispensing location, and
      a data receiver at the remote drug dispensing location that receives said selected drug and patient information.

2. The system of claim 1 where medical practitioner is certified to practice in a specific medical field and said listing of drugs is limited to said practitioner's specific medical field.

3. The system of claim 1 further comprising a node element in communication with said portable, hand held device that receives said selected drug prescription and patient information and transmits said drug prescription and patient information to said selected drug dispensing location.

4. The system of claim 1 further comprising a computer that receives said selected drug prescription and patient information and transmits, via a network, said drug prescription and patient information to said selected drug dispensing location.

5. The system of claim 1 where said listing of a plurality of prescription drugs applicable to said specific medical field is transmitted from a remote location to said device.

6. The system of claim 1 where said one or more drug dispensing locations is transmitted from a remote location to said device.

7. The system of claim 1 where said listing of drugs is limited to drugs available for prescription in a geographical region where the medical practitioner practices medicine.

8. The system of claim 1 where said listing of drugs is limited to drugs for treating symptoms of a patient.

9. The system of claim 1 where said listing of drugs is limited to drugs for treating an aliment of a patient.

10. The system of claim 1 where said portable, hand held device includes a removable memory that stores said listing of a plurality of prescription drugs.

11. The system of claim 1 where said portable, hand held device includes a removable memory that stores said one or more drug dispensing locations.

12. The system of claim 1 where said one or more drug dispensing locations are selected based on a geographical region.

13. The system of claim 1 where said data input mechanism includes a keyboard.

14. The system of claim 1 where said communication link comprises a radio transmitter, an infrared transmitter, a wired transmitter, or an ultrasonic transmitter.

15. The system of claim 1 where said portable, hand held device has
   a plurality of interactive screens retained in said memory, said screens to be displayed by said display, and
   a selector device enabling the medical practitioner to move from one screen to another.

16. A system for creating a prescription by a medical practitioner and communicating said prescription to a remote drug dispensing location, said system comprising:
   means for inputting data relating to a patient,
   means for storing (a) a listing of a plurality of prescription drugs, and (b) a listing of one or more drug dispensing locations,
   means for selecting one or more of the listed prescription drugs and one of said listed drug dispensing locations,
   means for transmitting said selected drug prescription and information identifying a patient to a selected drug dispensing location, and
   means for receiving a selected drug prescription and patient information at the remote drug dispensing location.

17. The system of claim 16 where the medical practitioner is certified to practice in a specific medical field and said listing of a plurality of prescription drugs is limited to said practitioner's specific medical field.

18. The system of claim 16 where said means for transmitting said selected drug prescription and patient data comprises:
   a node element that receives said selected drug prescription and patient information from said means for transmitting; and
   a processing node that receives said selected drug prescription and patient information from said node element and transmits said drug prescription and patient information to said selected drug dispensing location.

19. The system of claim 17 where said listing of drugs applicable to said specific medical field is transmitted from a remote location to said portable, hand held device.

20. The system of claim 16 where said listing of one or more drug dispensing locations is transmitted from a remote location to said portable, hand held device.

21. The system of claim 16 where said listing of drugs is limited to drugs available for prescription in a geographical region where the medical practitioner practices medicine.

22. The system of claim 16 where said listing of drugs is limited to drugs used to treat a specific symptom of a patient.

23. The system of claim 16 where said listing of drugs is limited to drugs used to treat a specific aliment of a patient.

24. The system of claim 16 further comprising a removable storing means for storing said listing of drugs.

25. The system of claim 16 further comprising a removable data storing means for storing said listing of one or more drug dispensing locations.

26. The system of claim 16 where said listing of one or more drug dispensing locations are selected based on a geographical region.

27. The system of claim 16 where said means for transmitting comprises a radio transmitter, an infrared transmitter, a wired transmitter, or an ultrasonic transmitter.

28. The system of claim 16 further comprising a means for displaying (a) said listing of a plurality of prescription drugs applicable, (b) patient information, and (c) said listing of one or more drug dispensing locations.

29. A portable, hand held device for creating a prescription by a medical practitioner and communicating said prescription to a drug dispensing location, said device comprising:
  a display;
  a memory that stores (a) a listing of a plurality of prescription drugs, and (b) one or more drug dispensing locations;
    a data input mechanism that enables the practitioner to enter information identifying a patient, select a drug dispensing location, select from the listing, one or more of the listed prescription drugs, and to enter a specific dose for said selected prescription drug, and
    a communication port that enables transmission of the prescription of said selected drug and patient information from said device to said drug dispensing location.

30. The device of claim 29 where the medical practitioner is certified to practice in a specific medical field and said listing of drugs is limited to said practitioner's specific medical field.

31. The device of claim 29 where said device communicates with a node element that receives said selected drug and patient information and transmits said drug and patient information to said selected drug dispensing location.

32. The device of claim 29 where said device communicates with a computer that receives said selected drug and patient information and transmits said drug and patient information to said selected drug dispensing location.

33. The device of claim 29 where said listing of a plurality of prescription drugs is transmitted from a computer to said device.

34. The device of claim 29 where said one or more drug dispensing locations is transmitted from a computer to said device.

35. The device of claim 29 where said listing of drugs is limited to drugs available in a geographical region where the medical practitioner practices medicine.

36. The device of claim 29 where said listing of drugs is limited to drugs associated as treating the symptoms of a patient.

37. The device of claim 29 where said listing of drugs is limited to drugs associated as treating an aliment of a patient.

38. The device of claim 29 where said device further comprises a removable memory that stores said listing of drugs.

39. The device of 29 where said device further comprises a removable memory that stores said listing of one or more drug dispensing locations.

40. The device of claim 29 where said listing of one or more drug dispensing locations are selected based on geographical region.

41. The device of claim 29 where said data input mechanism comprises a keyboard.

42. The device of claim 29 where said communication port is adapted to transmit to the drug dispensing location via wireless communication.

43. The device of claim 29 where there is a plurality of interactive screens retained in said memory to be displayed by said display and a selector device enabling the medical practitioner to move from one screen to another.

44. A portable, hand held device for creating a prescription by a medical practitioner certified to practice in a specific medical field and communicating said prescription and patient information to a drug dispensing location, said device comprising:
  means for inputting data relating to a patient;
  means for storing (a) a listing of a plurality of prescription drugs applicable to said specific medical field, (b) patient information, and (c) a grouping of one or more drug dispensing locations;
  means for selecting one or more of the listed prescription drugs and one of said drug dispensing locations; and
  means for transmitting a selected drug prescription and patient information to a selected drug dispensing location.

45. The device of claim 44 where said listing of a plurality of prescription drugs is limited to said practitioner's specific medical field.

46. The device of claim 44 where said means for transmitting said selected drug prescription and patient information comprises:
  a node element that receives said selected drug prescription and patient information from said means for transmitting; and
  a processing node that receives said selected drug prescription and patient information from said node element and transmits said drug prescription and patient information to said selected drug dispensing location.

47. The device of claim 44 where said listing of a plurality of prescription drugs applicable to said specific medical field is transmitted from a remote location to said device.

48. The device of claim 44 where said listing of one or more drug dispensing locations is transmitted from a remote location to said device.

49. The device of claim 44 where said listing of drugs is limited to drugs available for prescription in the geographical region where the medical practitioner practices medicine.

50. The device of claim 44 where said listing of drugs is limited to drugs used to treat a specific symptom of a patient.

51. The device of claim 44 where said listing of drugs is limited to drugs used to treat a specific aliment of a patient.

52. The device of claim 44 further comprising a removable storing means for storing said listing of drugs.

53. The device of claim 44 further comprising a removable data storing means for storing said listing of one or more drug dispensing locations.

54. The device of claim 44 where said listing of one or more drug dispensing locations are selected based on a geographical region.

55. The device of claim 44 where said means for transmitting comprises a radio transmitter, an infrared transmitter, a wired transmitter, or an ultrasonic transmitter.

56. The device of claim 44 further comprising a means for displaying (a) said listing of a plurality of prescription drugs applicable to said specific medical field, (b) patient information, and (c) said grouping of one or more drug dispensing locations.

57. A method of creating a prescription by a medical practitioner and communicating said prescription and patient information to a remote drug dispensing location, said method comprising:
(a) providing a portable, hand held device that enables said medical practitioner to (i) acquire information identifying a patient, (ii) select drugs from a list of drugs;
(b) creating a prescription from said selected drugs; and
(c) communicating said prescription and patient information to said remote drug dispensing location.

58. The method of claim 57 where acquiring patient information comprises the steps of:
querying whether said patient information is available on an accessible database; and
inputting the patient information if the patient information is not available on said accessible database.

59. The method of claim 57 where selecting drugs from a list of drugs comprises the steps of:
electronically coupling a database of said list of drugs to said device;
communicating with said database; and
selecting at least one drug from said database.

60. The method of claim 57 where selecting drugs from a list of drugs includes communicating with a computer that stores said list and selecting drugs from said list.

61. The method of claim 57 where of selecting drugs from a list of drugs comprises the steps of:
identifying patient symptoms;
inputting said patient symptoms in to said device;
providing a list drugs of drugs associated with treating said symptoms; and
selecting at least one drug from said list.

62. The method of claim 57 where selecting drugs from a list of drugs defined by the medical practitioner's field of practice comprises the steps of:
identifying a patient aliment;
inputting said patient aliment in to said device;
providing a list drugs of drugs associated with treating said aliment; and
selecting at least one drug from said list.

63. The method of claim 57 where said step of communicating said prescription and patient information to said remote drug dispensing location comprises the steps of:
electronically coupling a removable database of drug dispensing locations to said device;
communicating with said database;
retrieving at least one drug dispensing location from said database;
selecting a drug dispensing location; and
communicating said prescription to said drug dispensing location.

64. The method of claim 57 where said step of communicating said prescription and patient information to said drug dispensing location comprises the steps of:
communicating with a computer that stores a database of drug dispensing locations;
selecting a drug dispensing location from said database; and
communicating said prescription to said drug dispensing location.

65. The method of claim 57 where said drug dispensing location is selected from a database of drug dispensing locations and where said database is selected based on geographical region.

66. The method of claim 57 where said step of communicating said prescription to said drug dispensing location comprises the steps of:
wirelessly transmitting said prescription from said device to a wireless receiver;
transmitting said prescription from said wireless receiver to a computer; and
transmitting said prescription from said computer to said drug dispensing location.

67. The method of claim 66 where said wireless transmission comprises a radio transmission, an infrared transmission, or an ultrasonic transmission.

68. The method of claim 57 where the medical practitioner is certified to practice in a specific medical field and said listing of drugs is limited to said practitioner's specific medical field.

69. The method of claim 57 where said listing of drugs is limited to drugs available for prescription in a geographical region where the medical practitioner practices medicine.

* * * * *